US007925333B2

(12) United States Patent
Weir et al.

(10) Patent No.: US 7,925,333 B2
(45) Date of Patent: Apr. 12, 2011

(54) MEDICAL DEVICE INCLUDING SCANNED BEAM UNIT WITH OPERATIONAL CONTROL FEATURES

(75) Inventors: Michael P. Weir, Blanchester, OH (US); Robert J. Dunki-Jacobs, Mason, OH (US); Robert M. Trusty, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 754 days.

(21) Appl. No.: 11/846,039

(22) Filed: Aug. 28, 2007

(65) Prior Publication Data

US 2009/0062659 A1 Mar. 5, 2009

(51) Int. Cl.
*A61B 6/00* (2006.01)

(52) U.S. Cl. ........................................ 600/476

(58) Field of Classification Search .................. 600/476
See application file for complete search history.

(56) References Cited

U.S. PATENT DOCUMENTS 3,758,199 A 9/1973 Thaxter
3,959,582 A 5/1976 Law et al.
4,082,635 A 4/1978 Fritz et al.
4,141,362 A 2/1979 Wurster
4,313,431 A 2/1982 Frank
4,379,039 A 4/1983 Fujimoto et al.
4,403,273 A 9/1983 Nishioka
4,409,477 A 10/1983 Carl
4,421,382 A 12/1983 Doi et al.
4,524,761 A 6/1985 Hattori et al.
4,527,552 A 7/1985 Hattori
4,573,465 A 3/1986 Sugiyama et al.
4,576,999 A 3/1986 Eckberg
4,597,380 A 7/1986 Raif et al.
4,643,967 A 2/1987 Bryant
4,676,231 A 6/1987 Hisazumi et al.
4,760,840 A 8/1988 Fournier, Jr. et al.
4,803,550 A 2/1989 Yabe et al.
4,872,458 A 10/1989 Kanehira et al.
4,902,083 A 2/1990 Wells
4,902,115 A 2/1990 Takahashi (Continued)

FOREIGN PATENT DOCUMENTS

DE 3837248 5/1990

(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Eric F Winakur
*Assistant Examiner* — Hien Nguyen
(74) *Attorney, Agent, or Firm* — Victor C. Moreno

(57) ABSTRACT

A method of controlling a medical device is provided. The method includes generating a beam of radiation using a radiation source assembly. The beam of radiation is directed toward a distal end of the medical device using an optical fiber. The beam of radiation is directed onto an area of interest by scanning the reflector in a scanning pattern, the reflector receiving the beam of radiation from the optical fiber. Radiation is collected from the area of interest using a collector to generate a signal for use in producing a viewable image. A loss of scan condition of the reflector is detected automatically by a control system.

21 Claims, 10 Drawing Sheets

U.S. PATENT DOCUMENTS 4,934,773 A 6/1990 Becker
4,938,205 A 7/1990 Nudelman
5,003,300 A 3/1991 Wells
5,023,905 A 6/1991 Wells et al.
5,048,077 A 9/1991 Wells et al.
5,074,860 A 12/1991 Gregory et al.
5,078,150 A 1/1992 Hara et al.
5,163,936 A 11/1992 Black et al.
5,163,945 A 11/1992 Ortiz et al.
5,172,685 A 12/1992 Nudelman
5,192,288 A 3/1993 Thompson et al.
5,200,819 A 4/1993 Nudelman et al.
5,200,838 A 4/1993 Nudelman et al.
5,207,670 A 5/1993 Sinofsky
5,218,195 A 6/1993 Hakamata
5,251,025 A 10/1993 Cooper et al.
5,251,613 A 10/1993 Adair
5,269,289 A 12/1993 Takehana et al.
5,318,024 A 6/1994 Kittrell et al.
5,334,991 A 8/1994 Wells et al.
5,368,015 A 11/1994 Wilk
5,370,643 A 12/1994 Krivoshlykov et al.
5,387,197 A 2/1995 Smith et al.
5,393,647 A 2/1995 Neukermans et al.
5,436,655 A 7/1995 Hiyama et al.
5,467,104 A 11/1995 Furness, III et al.
5,488,862 A 2/1996 Neukermans et al.
5,531,740 A 7/1996 Black
5,545,211 A 8/1996 An et al.
5,552,452 A 9/1996 Khadem et al.
5,557,444 A 9/1996 Melville et al.
5,590,660 A 1/1997 MacAulay et al.
5,596,339 A 1/1997 Furness, III et al.
5,608,451 A 3/1997 Konno et al.
5,629,790 A 5/1997 Neukermans et al.
5,648,618 A 7/1997 Neukermans et al.
5,649,952 A 7/1997 Lam
5,657,165 A 8/1997 Karpman et al.
5,658,710 A 8/1997 Neukermans
5,659,327 A 8/1997 Furness, III et al.
5,694,237 A 12/1997 Melville
5,701,132 A 12/1997 Kollin et al.
5,713,891 A 2/1998 Poppas
5,728,121 A 3/1998 Bimbo et al.
5,735,792 A 4/1998 Vanden Hoek et al.
5,742,419 A 4/1998 Dickensheets et al.
5,742,421 A 4/1998 Wells et al.
5,751,465 A 5/1998 Melville et al.
5,768,461 A 6/1998 Svetkoff et al.
5,797,944 A 8/1998 Nobles et al.
5,817,061 A 10/1998 Goodwin et al.
5,823,943 A 10/1998 Tomioka et al.
5,827,176 A 10/1998 Tanaka et al.
5,827,190 A 10/1998 Palcic et al.
5,841,553 A 11/1998 Neukermans
5,861,549 A 1/1999 Neukermans et al.
5,867,297 A 2/1999 Kiang et al.
5,895,866 A 4/1999 Neukermans et al.
5,903,397 A 5/1999 Melville et al.
5,907,425 A 5/1999 Dickensheets et al.
5,913,591 A 6/1999 Melville
5,947,930 A 9/1999 Schwemberger et al.
5,969,465 A 10/1999 Neukermans et al.
5,969,871 A 10/1999 Tidwell et al.
5,982,528 A 11/1999 Melville
5,982,555 A 11/1999 Melville et al.
5,993,037 A 11/1999 Tomioka et al.
5,995,264 A 11/1999 Melville
6,007,208 A 12/1999 Dickensheets et al.
6,008,781 A 12/1999 Furness, III et al.
6,013,025 A 1/2000 Bonne et al.
6,016,440 A 1/2000 Simon et al.
6,017,356 A 1/2000 Frederick et al.
6,017,603 A 1/2000 Tokuda et al.
6,024,744 A 2/2000 Kese et al.
6,043,799 A 3/2000 Tidwell
6,044,705 A 4/2000 Neukermans et al.
6,046,720 A 4/2000 Melville et al.
6,049,407 A 4/2000 Melville
6,056,721 A 5/2000 Shulze
6,057,952 A 5/2000 Kubo et al.
6,059,720 A 5/2000 Furusawa et al.
6,061,163 A 5/2000 Melville
6,064,779 A 5/2000 Neukermans et al.
6,069,725 A 5/2000 Melville
6,086,528 A 7/2000 Adair
6,086,531 A 7/2000 Tomioka et al.
6,088,145 A 7/2000 Dickensheets et al.
6,097,353 A 8/2000 Melville et al.
6,122,394 A 9/2000 Neukermans et al.
6,139,175 A 10/2000 Tomioka et al.
6,140,979 A 10/2000 Gerhard et al.
6,151,167 A 11/2000 Melville
6,154,305 A 11/2000 Dickensheets et al.
6,154,321 A 11/2000 Melville et al.
6,157,352 A 12/2000 Kollin et al.
6,166,841 A 12/2000 Melville
6,172,789 B1 1/2001 Kino et al.
6,178,346 B1 1/2001 Amundson et al.
6,179,776 B1 1/2001 Adams et al.
6,191,761 B1 2/2001 Melville et al.
6,192,267 B1 2/2001 Scherninski et al.
6,200,595 B1 3/2001 Motoyashiki et al.
6,204,829 B1 3/2001 Tidwell
6,204,832 B1 3/2001 Melville et al.
6,207,392 B1 3/2001 Weiss et al.
6,210,401 B1 4/2001 Lai
6,220,711 B1 4/2001 Melville
6,221,068 B1 4/2001 Fried et al.
6,229,139 B1 5/2001 Neukermans et al.
6,235,017 B1 5/2001 Jegorov et al.
6,243,186 B1 6/2001 Melville
6,245,590 B1 6/2001 Wine et al.
6,256,131 B1 7/2001 Wine et al.
6,257,727 B1 7/2001 Melville
6,272,907 B1 8/2001 Neukermans et al.
6,276,798 B1 8/2001 Gil et al.
6,281,862 B1 8/2001 Tidwell et al.
6,284,185 B1 9/2001 Tokuda et al.
6,285,489 B1 9/2001 Helsel et al.
6,285,505 B1 9/2001 Melville et al.
6,288,816 B1 9/2001 Melville et al.
6,292,287 B1 9/2001 Fujinoki
6,293,911 B1 9/2001 Imaizumi et al.
6,294,239 B1 9/2001 Tokuda et al.
6,294,775 B1 9/2001 Seibel et al.
6,317,103 B1 11/2001 Furness, III et al.
6,323,037 B1 11/2001 Lauto et al.
6,324,007 B1 11/2001 Melville
6,327,493 B1 12/2001 Ozawa et al.
6,331,909 B1 12/2001 Dunfield
6,333,110 B1 12/2001 Barbera-Guillem
6,338,641 B2 1/2002 Nicholls
6,352,344 B2 3/2002 Tidwell
6,353,183 B1 3/2002 Ott et al.
6,362,912 B1 3/2002 Lewis et al.
6,364,829 B1 4/2002 Fulghum
6,369,928 B1 4/2002 Mandella et al.
6,369,953 B2 4/2002 Melville et al.
6,369,954 B1 4/2002 Berge et al.
6,370,406 B1 4/2002 Wach et al.
6,370,422 B1 4/2002 Richards-Kortum et al.
6,373,995 B1 4/2002 Moore
6,384,406 B1 5/2002 Wine et al.
6,388,641 B2 5/2002 Tidwell et al.
6,392,220 B1 5/2002 Slater et al.
6,396,461 B1 5/2002 Lewis et al.
6,414,779 B1 7/2002 Mandella et al.
6,417,502 B1 7/2002 Stoner et al.
6,423,956 B1 7/2002 Mandella et al.
6,425,900 B1 7/2002 Knodel et al.
6,426,013 B1 7/2002 Neukermans et al.
6,433,907 B1 8/2002 Lippert et al.
6,435,637 B1 8/2002 Lyman
6,441,356 B1 8/2002 Mandella et al.
6,445,362 B1 9/2002 Tegreene
6,447,524 B1 9/2002 Knodel et al.

6,462,770 B1 10/2002 Cline et al.
6,464,363 B1 10/2002 Nishioka et al.
6,467,345 B1 10/2002 Neukermans et al.
6,470,124 B1 10/2002 Le Gargasson et al.
6,477,403 B1 11/2002 Eguchi et al.
6,478,809 B1 11/2002 Brotz
6,485,413 B1 11/2002 Boppart et al.
6,492,962 B2 12/2002 Melville et al.
6,494,578 B1 12/2002 Plummer et al.
6,503,196 B1 1/2003 Kehr et al.
6,510,338 B1 1/2003 Irion et al.
6,512,622 B2 1/2003 Wine et al.
6,513,939 B1 2/2003 Fettig et al.
6,515,278 B2 2/2003 Wine et al.
6,515,781 B2 2/2003 Lewis et al.
6,520,972 B2 2/2003 Peters
6,522,444 B2 2/2003 Mandella et al.
6,525,310 B2 2/2003 Dunfield
6,527,708 B1 3/2003 Nakamura et al.
6,529,770 B1 3/2003 Grimblatov
6,530,698 B1 3/2003 Kuhara et al.
6,535,183 B2 3/2003 Melville et al.
6,535,325 B2 3/2003 Helsel et al.
6,537,211 B1 3/2003 Wang et al.
6,538,625 B2 3/2003 Tidwell et al.
6,545,260 B1 4/2003 Katashiro et al.
6,560,028 B2 5/2003 Melville et al.
6,563,105 B2 5/2003 Seibel et al.
6,563,106 B1 5/2003 Bowers et al.
6,572,606 B2 6/2003 Kliewer et al.
6,583,117 B2 6/2003 Owen et al.
6,583,772 B1 6/2003 Lewis et al.
6,585,642 B2 7/2003 Christopher
6,603,552 B1 8/2003 Cline et al.
6,608,297 B2 8/2003 Neukermans et al.
6,639,570 B2 10/2003 Furness, III et al.
6,639,719 B2 10/2003 Tegreene et al.
6,650,877 B1 11/2003 Tarbouriech et al.
6,653,621 B2 11/2003 Wine et al.
6,654,158 B2 11/2003 Helsel et al.
6,661,393 B2 12/2003 Tegreene et al.
6,674,993 B1 1/2004 Tarbouriech
6,685,804 B1 2/2004 Ikeda et al.
6,687,034 B2 2/2004 Wine et al.
6,689,056 B1 2/2004 Kilcoyne et al.
6,699,170 B1 3/2004 Crocker et al.
6,700,552 B2 3/2004 Kollin et al.
6,714,331 B2 3/2004 Lewis et al.
6,734,835 B2 5/2004 Tidwell et al.
6,736,511 B2 5/2004 Plummer et al.
6,741,884 B1 5/2004 Freeman et al.
6,749,346 B1 6/2004 Dickensheets et al.
6,755,536 B2 6/2004 Tegreene et al.
6,762,867 B2 7/2004 Lippert et al.
6,768,588 B2 7/2004 Urey
6,771,001 B2 8/2004 Mao et al.
6,782,748 B2 8/2004 Weber et al.
6,786,382 B1 9/2004 Hoffman
6,795,221 B1 9/2004 Urey
6,802,809 B2 10/2004 Okada
6,803,561 B2 10/2004 Dunfield
6,821,245 B2 11/2004 Cline et al.
6,845,190 B1 1/2005 Smithwick et al.
6,856,436 B2 2/2005 Brukilacchio et al.
6,856,712 B2 2/2005 Fauver et al.
6,879,428 B2 4/2005 Massieu
6,888,552 B2 5/2005 Debevec et al.
6,894,823 B2 5/2005 Taylor et al.
6,899,675 B2 5/2005 Cline et al.
6,902,527 B1 6/2005 Doguchi et al.
6,905,057 B2 6/2005 Swayze et al.
6,939,364 B1 9/2005 Soltz et al.
6,957,898 B2 10/2005 Yu
6,967,757 B1 11/2005 Allen et al.
6,974,472 B2 12/2005 Hong et al.
6,975,898 B2 12/2005 Seibel et al.
6,976,994 B2 12/2005 Ballou et al.
6,978,921 B2 12/2005 Shelton, IV et al.
6,985,271 B2 1/2006 Yazdi et al.
6,991,602 B2 1/2006 Nakazawa et al.
7,005,195 B2 2/2006 Cheng et al.
7,009,634 B2 3/2006 Iddan et al.
7,013,730 B2 3/2006 Malametz
7,015,956 B2 3/2006 Luo et al.
7,018,401 B1 3/2006 Hyodoh et al.
7,023,402 B2 4/2006 Lewis et al.
7,025,777 B2 4/2006 Moore
7,033,348 B2 4/2006 Alfano et al.
7,035,777 B2 4/2006 Araki et al.
7,061,450 B2 6/2006 Bright et al.
7,065,301 B2 6/2006 Shastri et al.
7,066,879 B2 6/2006 Fowler et al.
7,071,594 B1 7/2006 Yan et al.
7,071,931 B2 7/2006 Tegreene et al.
7,078,378 B1 7/2006 Owen et al.
7,108,656 B2 9/2006 Fujikawa et al.
7,112,302 B2 9/2006 Yoshimi et al.
7,126,903 B2 10/2006 Feenstra et al.
7,189,961 B2 3/2007 Johnston et al.
7,190,329 B2 3/2007 Lewis et al.
7,232,071 B2 6/2007 Lewis et al.
7,271,383 B2 9/2007 Chee
7,391,013 B2 6/2008 Johnston et al.
2001/0055462 A1 12/2001 Seibel
2002/0015724 A1 2/2002 Yang et al.
2002/0024495 A1 2/2002 Lippert et al.
2002/0050956 A1 5/2002 Gerhard et al.
2002/0075284 A1 6/2002 Rabb, III
2002/0088925 A1 7/2002 Nestorovic et al.
2002/0115922 A1 8/2002 Waner et al.
2002/0141026 A1 10/2002 Wiklof et al.
2002/0158814 A1 10/2002 Bright et al.
2002/0163484 A1 11/2002 Furness, III et al.
2002/0167462 A1 11/2002 Lewis et al.
2002/0171776 A1 11/2002 Tegreene et al.
2002/0171937 A1 11/2002 Tegreene et al.
2003/0016187 A1 1/2003 Melville et al.
2003/0030753 A1 2/2003 Kondo et al.
2003/0032143 A1 2/2003 Neff et al.
2003/0034709 A1 2/2003 Jerman
2003/0058190 A1 3/2003 Lewis et al.
2003/0086172 A1 5/2003 Urey
2003/0092995 A1 5/2003 Thompson
2003/0130562 A1 7/2003 Barbato et al.
2003/0142934 A1 7/2003 Pan et al.
2003/0159447 A1 8/2003 Sergio et al.
2003/0214460 A1 11/2003 Kovacs
2003/0216729 A1 11/2003 Marchitto et al.
2004/0004585 A1 1/2004 Brown et al.
2004/0057103 A1 3/2004 Bernstein
2004/0075624 A1 4/2004 Tegreene et al.
2004/0076390 A1 4/2004 Dong Yang et al.
2004/0085261 A1 5/2004 Lewis et al.
2004/0085617 A1 5/2004 Helsel et al.
2004/0087844 A1 5/2004 Yen
2004/0101822 A1 5/2004 Wiesner et al.
2004/0113059 A1 6/2004 Kawano et al.
2004/0118821 A1 6/2004 Han et al.
2004/0119004 A1 6/2004 Wine et al.
2004/0122328 A1 6/2004 Wang et al.
2004/0133786 A1 7/2004 Tarbouriech
2004/0151466 A1 8/2004 Crossman-Bosworth et al.
2004/0155186 A1 8/2004 Nestorovic et al.
2004/0155834 A1 8/2004 Wit et al.
2004/0179254 A1 9/2004 Lewis et al.
2004/0196518 A1 10/2004 Wine et al.
2004/0223202 A1 11/2004 Lippert et al.
2004/0225222 A1 11/2004 Zeng et al.
2004/0236371 A1 11/2004 McNally-Heintzelman et al.
2004/0240866 A1 12/2004 Ramsbottom
2004/0252377 A1 12/2004 Urey
2004/0254474 A1 12/2004 Seibel et al.
2005/0010787 A1 1/2005 Tarbouriech
2005/0014995 A1 1/2005 Amundson et al.
2005/0020877 A1* 1/2005 Ishihara et al. ............... 600/109
2005/0020926 A1* 1/2005 Wiklof et al. ................ 600/476
2005/0023356 A1 2/2005 Wiklof et al.
2005/0030305 A1 2/2005 Brown et al.

| | | | | |
|---|---|---|---|---|
| 2005/0038322 | A1 | 2/2005 | Banik | |
| 2005/0116038 | A1 | 6/2005 | Lewis et al. | |
| 2005/0162762 | A1 | 7/2005 | Novak | |
| 2005/0187441 | A1 | 8/2005 | Kawasaki et al. | |
| 2005/0203343 | A1 | 9/2005 | Kang et al. | |
| 2005/0240147 | A1 | 10/2005 | Makower et al. | |
| 2006/0010985 | A1 | 1/2006 | Schneider | |
| 2006/0084867 | A1 | 4/2006 | Tremblay et al. | |
| 2006/0164330 | A1 | 7/2006 | Bright et al. | |
| 2006/0183246 | A1 | 8/2006 | Wiesner et al. | |
| 2006/0195014 | A1 | 8/2006 | Seibel et al. | |
| 2006/0238774 | A1 | 10/2006 | Lindner et al. | |
| 2006/0241562 | A1 * | 10/2006 | John et al. | 604/503 |
| 2006/0245971 | A1 | 11/2006 | Burns et al. | |
| 2006/0284790 | A1 | 12/2006 | Tegreene et al. | |
| 2007/0038119 | A1 | 2/2007 | Chen et al. | |
| 2007/0046778 | A1 | 3/2007 | Ishihara et al. | |
| 2007/0135770 | A1 | 6/2007 | Hunt et al. | |
| 2007/0156021 | A1 | 7/2007 | Morse et al. | |
| 2007/0161876 | A1 | 7/2007 | Bambot et al. | |
| 2007/0162093 | A1 | 7/2007 | Porter et al. | |
| 2007/0167681 | A1 | 7/2007 | Gill et al. | |
| 2007/0173707 | A1 | 7/2007 | Mitra | |
| 2007/0179366 | A1 | 8/2007 | Pewzner et al. | |
| 2007/0197874 | A1 | 8/2007 | Ishihara | |
| 2007/0197875 | A1 | 8/2007 | Osaka | |
| 2007/0203413 | A1 | 8/2007 | Frangioni | |
| 2007/0213588 | A1 | 9/2007 | Morishita et al. | |
| 2007/0213618 | A1 | 9/2007 | Li et al. | |
| 2007/0225695 | A1 | 9/2007 | Mayer et al. | |
| 2007/0238930 | A1 | 10/2007 | Wiklof et al. | |
| 2007/0244365 | A1 | 10/2007 | Wiklof | |
| 2007/0260121 | A1 | 11/2007 | Bakos et al. | |
| 2007/0260273 | A1 | 11/2007 | Cropper et al. | |
| 2008/0058629 | A1 | 3/2008 | Seibel et al. | |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.com (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PIxBead™ Superior Qualities," http:www.crystalplex.com (date of first publication unknown).
"Microvision [illuminating information] Products/Overview, Corporate Overview Presentation 2006" (2006).
"Holographic Beam Combiner for Ladar, Printer, Fiber Optics, and Cancer Treatment," by Digital Optics Technologies, Inc., http://www.mdatechnology.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarzing Cube Beamsplitters," from GlobalSpec The Engineering Search Engine, http://www.globalspec.com (date of first publication unknown).
Literature entitled "Dallas Semiconductor MAXIM—Visible-Laser Driver has Digitally Controlled Power Modulation," by Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, The Netherlands (Sep. 12-14, 2005).
"Bladeless Trocars," by Johnson & Johnson, http://wwvv.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
Ra, H. et al., "Biomedical Optics & Medical Imaging—Microtechnology enables endoscopic confocal microscopy," SPIE (http://spie.org) (2007).
Invitation to Pay Additional Fees with Partial International Search Report, PCT/US2008/074275 (Jan. 16, 2009).
Invitation to Pay Additional Fees with Partial International Search Report, PCT/US2008/074273 (Dec. 30, 2008).
International Search Report issued regarding International Application No. PCT/US2007/078868 (Mar. 28, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
PCT, International Search Report, PCT/US2008/066552 (Oct. 23, 2008).

* cited by examiner

MEDICAL DEVICE INCLUDING SCANNED BEAM UNIT WITH OPERATIONAL CONTROL FEATURES

TECHNICAL FIELD

The present application relates generally to medical devices and in particular to a medical device including a scanned beam unit with operational control features.

BACKGROUND

Imaging devices may be used to provide visualization of a site on or within a patient, or in other areas of use. One such device is described in U.S. Patent Publication Number 2005/0020926; corresponding to U.S. application Ser. No. 10/873,540, filed on Jun. 21, 2004, the entire contents of which are hereby incorporated by reference as if fully set forth herein. In such systems a scanned beam imaging system may utilize a radiation source or sources. The radiation is scanned onto or across an area of interest by an oscillating mirror. The radiation is reflected, scattered, refracted or otherwise perturbed by the illuminated area. The perturbed radiation is then gathered/sensed and converted into electrical signals that are processed to generate a viewable image.

SUMMARY

In an aspect, a method of controlling a medical device is provided. The method includes generating a beam of radiation using a radiation source assembly. The beam of radiation is directed toward a distal end of the medical device using an optical fiber. The beam of radiation is directed onto an area of interest by scanning the reflector in a scanning pattern, the reflector receiving the beam of radiation from the optical fiber. Radiation is collected from the area of interest using a collector to generate a signal for use in producing a viewable image. A loss of scan condition of the reflector is detected automatically by a control system.

In another aspect, a medical device includes a radiation source assembly including a radiation source configured to generate a beam of radiation. An optical fiber directs the beam from the radiation source assembly toward a distal end of the medical device. A reflector receives the beam from the optical fiber. The reflector is configured to direct the beam onto an area of interest by scanning in a scanning pattern. A collector is arranged and configured to receive radiation from the area of interest to generate a signal for use in producing a viewable image. A filter is responsive to signal components corresponding to scanning frequencies. The filter is configured to produce an output based on the signal components. A comparator is adapted to provide an indication when the output of the filter exceeds or is below a predetermined limit.

In another aspect, a medical device includes a radiation source assembly including a radiation source configured to generate a beam of radiation. An optical fiber directs the beam from the radiation source assembly toward a distal end of the medical device. A reflector receives the beam from the optical fiber. The reflector is configured to direct the beam onto an area of interest by scanning in a scanning pattern. A comb motor drive is operatively connected to the reflector for driving the reflector in the scanning pattern. An impedance meter is connected to comb motor drive. The impedance meter is configured to determine an instantaneous impedance to the motor comb drive for use in determining if the reflector is scanning.

In another aspect, a medical device includes a radiation source assembly including a radiation source configured to generate a beam of radiation. An optical fiber directs the beam from the radiation source assembly toward a distal end of the medical device along a path defined by the optical fiber. A reflector receives the beam from the optical fiber. The reflector is configured to direct the beam onto an area of interest by scanning in a scanning pattern. A collector is arranged and configured to receive radiation from the area of interest to generate a signal for use in producing a viewable image. A beam splitter is arranged and configured to separate reflected radiation from the path traveling through the optical fiber from the distal end of the medical device toward a proximal end of the medical device.

In another aspect, a medical device includes a radiation source assembly including a radiation source configured to generate a beam for treatment of a medical condition. An optical fiber directs the beam from the radiation source assembly toward a distal end of the medical device. A reflector receives the beam from the optical fiber. The reflector is configured to direct the beam onto an area of interest by scanning in a scanning pattern. A means for determining if the reflector is scanning is provided.

In another aspect, a medical device includes a radiation source assembly including a radiation source configured to generate a beam for treatment of a medical condition. An optical fiber directs the beam from the radiation source assembly toward a distal end of the medical device. A reflector receives the beam from the optical fiber. The reflector is configured to direct the beam onto an area of interest by scanning in a scanning pattern. A control system is configured to control the radiation source by detecting an insertion or retraction of the medical device into a body cavity.

The details of one or more embodiments of the invention are set forth in the accompanying drawings and the description below. Other features, objects, and advantages of the invention will be apparent from the description and the drawings, and from the claims.

DETAILED DESCRIPTION

Before explaining the several expressions of embodiments of the present invention in detail, it should be noted that each is not limited in its application or use to the details of construction and arrangement of parts illustrated in the accompanying drawings and description. The illustrative expressions of embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described expressions of embodiments, examples, etc. can be combined with any one or more of the other following-described expressions of embodiments, examples, etc.

Figure 1:
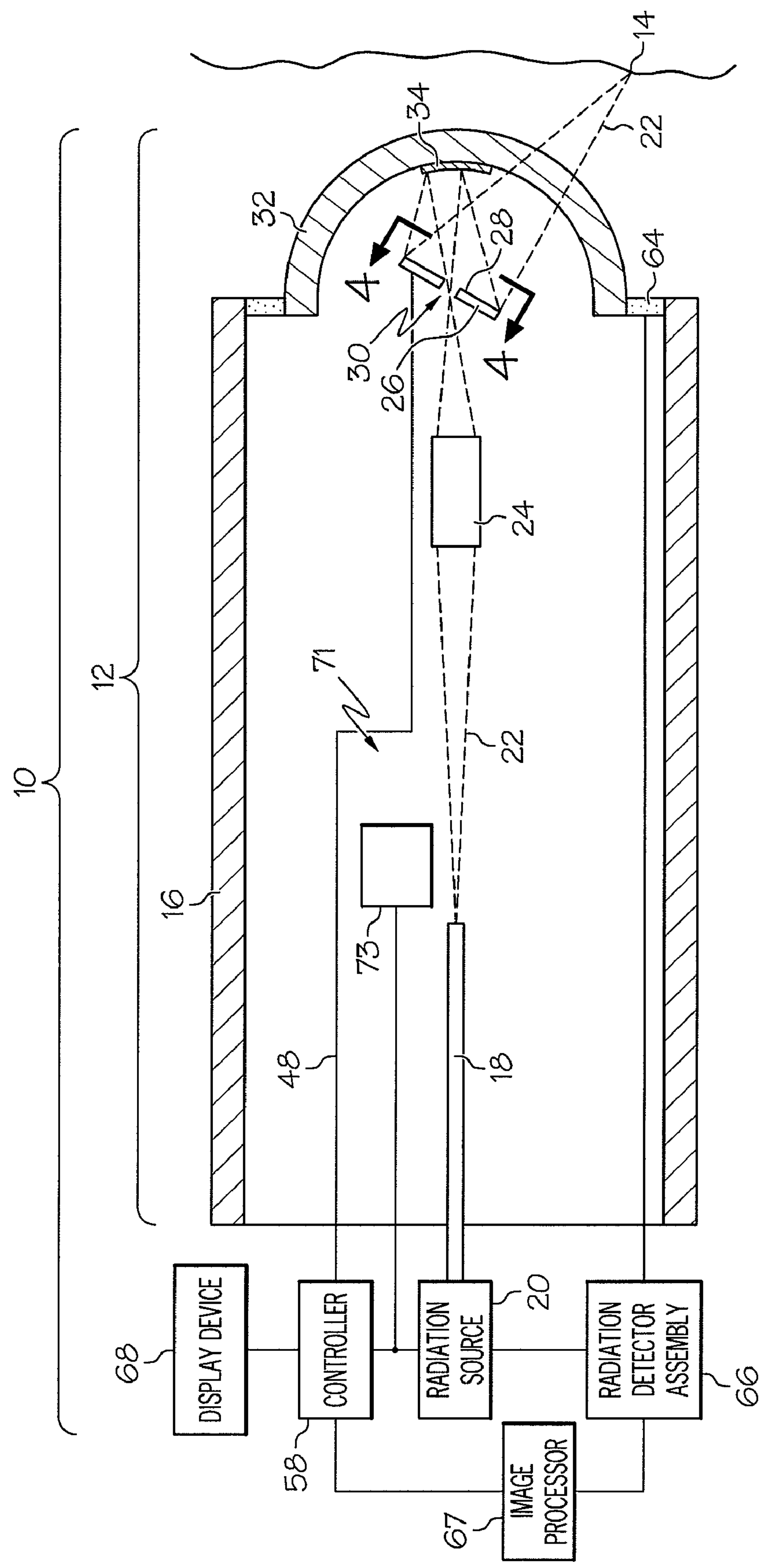
FIG. 1 is a side cross section and schematic representation of one embodiment of a scanning assembly.

As shown in FIG. 1, a scanning assembly, generally designated 10, includes a scanning unit 12 configured to direct radiation onto an area of interest 14. The area of interest 14 may be located on or inside the body of a human or animal patient, but could also be nearly any area which is desired to be scanned/visualized. The scanning unit 12 (or other components or subcomponents) can then collect the radiation that is reflected, scattered, refracted or otherwise perturbed or affected (hereinafter referred to as radiation that is "returned from" the illuminated area 14) by the area 14 receiving radiation. The collected radiation can then be analyzed and processed to generate an image of the illuminated area 14.

The scanning unit 12 includes a housing 16 which receives a source fiber 18 therein. In the illustrated embodiment the housing 16 is generally cylindrical (see FIG. 2) and sized to be gripped and manually manipulated, although the housing 16 can take any of a variety of forms, shapes and sizes. The source fiber 18 is operatively coupled to a radiation source 20 to transmit radiation from the radiation source 20 to a position inside of the housing 16 or adjacent to a reflector 26. The radiation source 20 can take any of a variety of forms, including light emitting diodes (LEDs), lasers, thermal sources, arc sources, fluorescent sources, gas discharge sources, other sources, or combinations of these sources. The radiation provided by the radiation source 20 can include energy in the visible light spectrum, such as red, green, or blue radiation, or various combinations thereof, although the radiation need not necessarily be within the visible spectrum. The source fiber 18 may take the form of one or more optical fibers, or various other energy transmission means sufficient to transmit radiation from the radiation source 20.

Figure 3:
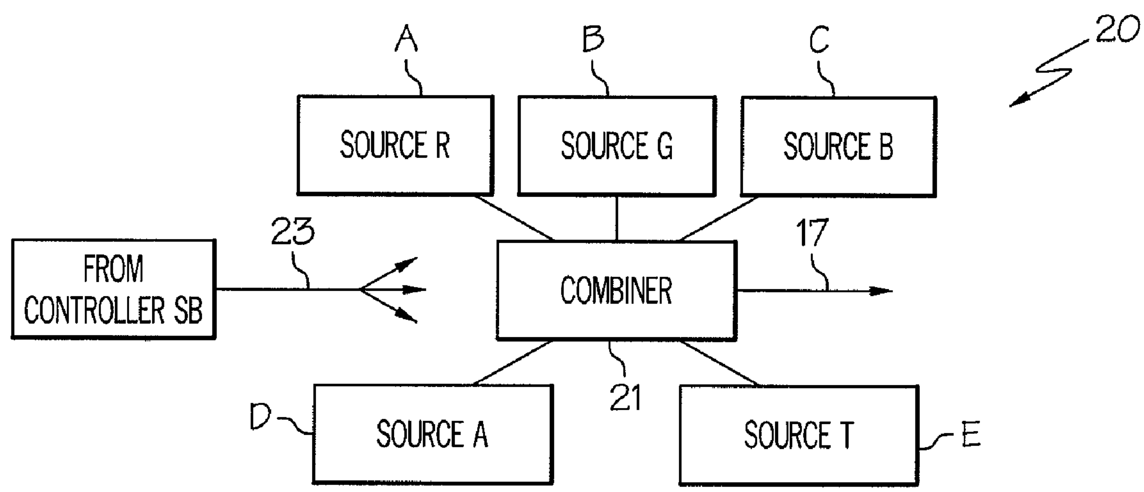
FIG. 3 is a diagrammatic view of an embodiment of a radiation source assembly of the scanning assembly of FIG. 1.

FIG. 3 is a block diagram of one implementation of the radiation source 20. The radiation source 20 includes multiple sources, each capable of generating radiation at a selected wavelength. Five sources are shown here, denoted A thru E. The outputs of the radiation sources A-E may, in some embodiments, be brought together in combiner element 21 to yield an output beam 17. Combiner 21 may also include beam-shaping optics such as one or more collimating lenses and/or apertures. The sources may be of various types such as, for instance, light emitting diodes (LEDs), lasers, thermal sources, arc sources, fluorescent sources, gas discharge sources, or others. Signals 23 may be provided by controller 58 (FIG. 1) to one or more of the sources and optionally the combiner 21. Signals 23 may optionally control wavelength, power, modulation or other beam properties. The wavelength of radiation, for example, may be selected for imaging and/or therapy. An "imaging beam" refers to radiation selected for use in creating an image of a surface or region and a "therapeutic beam" refers to radiation selected to provide treatment of a condition such as diseased or damaged tissue. In this example, sources A, B and C emit red, green and blue radiation; source D emits an aiming beam at a wavelength selected to yield a distinct contrast to the typical target material; and source E emits a therapeutic beam at a wavelength that is highly absorbed and moreover can be efficiently generated at high power to treat diseased or damaged tissue. In some embodiments, the aiming beam may be provided by source separate from the therapeutic beam source E. As an alternative, an aiming beam may be provided by source E as a reduced power therapeutic beam. Details of delivering therapeutic and imaging beams using a scanning assembly are described in greater detail in pending U.S. patent application Ser. No. 11/716,806, filed Mar. 12, 2007, entitled MEDICAL DEVICE INCLUDING SCANNED BEAM UNIT FOR IMAGING AND THERAPY, the details of which are hereby incorporated by reference as if fully set forth herein.

Referring back to FIG. 1, the end of the source fiber 18 may be shaped or polished to create a beam 22 of known divergence. After exiting the source fiber 18 the beam 22 may pass through, and be shaped by a lens or other optics 24 to create a desired beam shape. In other embodiments, the beam 22 may not pass through and be shaped by a lens or other optic to create the desired beam shape. The scanning unit 12 includes the mirror or reflector 26 at or adjacent to its distal end. The reflector 26 may take the form of a micromirror or other reflective surface. The reflector 26 thus may take the form of or include a microelectrical mechanical system ("MEMS") manufactured using standard MEMS techniques. The reflector 26 may include a semiconductor substrate, such as silicon, with a reflective outer surface, such as gold or other suitable material, forming its outer reflective surface 28. However the surface 28 may take various other forms, such as a multilayer dielectric coating.

In the illustrated embodiment, the reflector 26 includes a central aperture 30 that is positioned to allow the beam 22 to pass therethrough. However, the reflector 26 and scanning unit 12 can take any of a variety of shapes and configurations besides that shown herein. For example, rather than including a central aperture 30 that allows the beam 22 to pass therethrough, the beam 22 may be laterally offset from the reflector 26, and guided to the reflector 26 by another mirror/reflector.

After passing through the aperture 30 of the reflector 26, the beam 22 approaches an optical element 32 that is positioned at a distal end of the scanning unit 12. The optical element 32 can be generally hemispherical and is typically referred to as a dome. However, the shape, curvature, contour, and surface treatment of the optical element 32 may vary depending on the desired application/use of the scanning unit 12 and the desired optical properties of the optical element 32. The optical element 32 may form a hermetic seal with the housing 16 to protect the internal elements of the scanning unit 12 from the surrounding environment.

The optical element 32 may include a reflecting surface 34 on its inner surface. The reflecting surface 34 may be directly deposited on the inner surface of the optical element 32, or integrated into the optical element 32, or can take the form of a separate and discrete element coupled to the optical element 32. After the beam 22 passes through the aperture 30 of the reflector 26, the beam 22 impinges upon the reflecting surface 34 which reflects the beam 22 and re-directs the beam 22 toward the reflector 26. The inner surface of the optical element 32 and/or the reflecting surface 34 may also shape the beam 22 as desired due to the shape or curvature of the reflecting surface 34. If the beam 22 is laterally offset from the center of the scanning unit 12 in the arrangement briefly described above, the reflecting surface 34 on the optical element 32 may be omitted.

Figure 4:
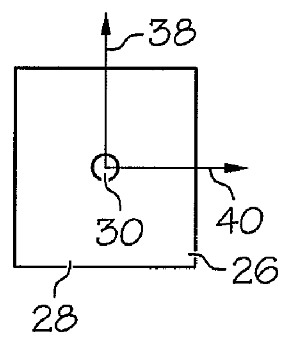
FIG. 4 is a front view taken along line 4-4 of FIG. 1.
Figure 5:
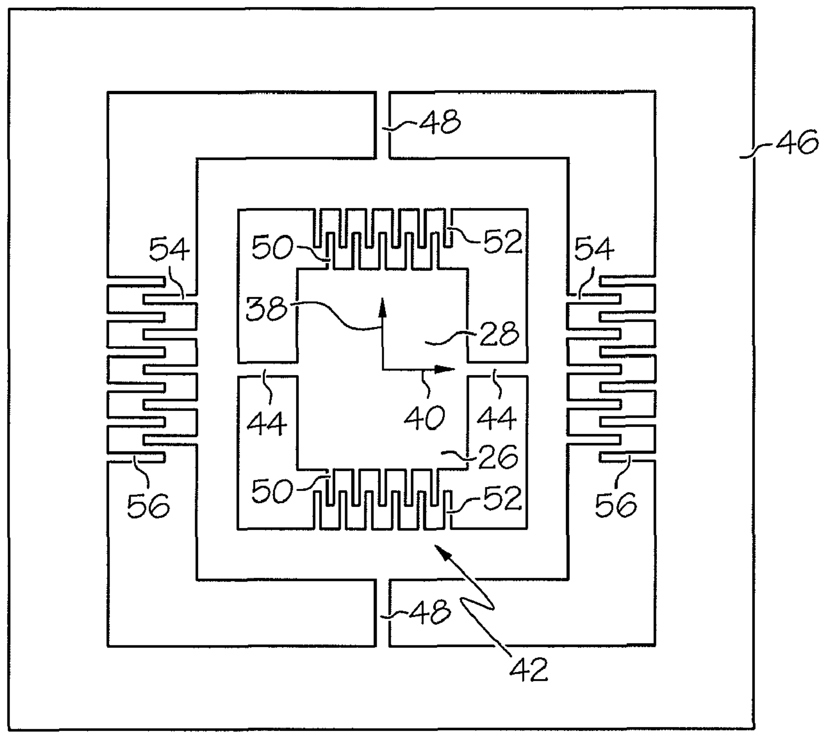
FIG. 5 is a front view of a drive mechanism usable with the scanning assembly of FIG. 1.

The reflector 26 may be independently oscillatable/movable about two orthogonal axes, such as axes 38, 40 shown in FIGS. 4 and 5. As shown in FIG. 5, the reflector 26 may be coupled to an inner support structure 42, that generally surrounds the reflector 26, by a pair of opposed, generally aligned torsion arms 44. The inner support structure 42 is coupled to an outer support structure 46, that generally surrounds the inner support structure 42, by a pair of opposed, generally aligned torsion arms 48. The outer torsion arms 48 are generally perpendicular to the inner torsion arms 44. Thus the reflector 26 may double gimbaled or otherwise pivotable about the two axes 38, 40 to position the reflector 26 as desired.

The inner support structure 42 may have a pair of opposed comb structures 50 that are interleaved with comb structures 52 of the reflector 26. Similarly, the outer support structure 46 may have a pair of opposed comb structures 54 that are interleaved with comb structures 56 of the inner support structure 42. A voltage can be applied to one or both comb structures 50, 52 which causes the reflector 26 to pivot about arms 44/axis 40. Similarly, a voltage can be applied to one or both comb structures 54, 56 to cause the reflector 26 to pivot about arms 48/axis 38. The voltages can be applied by a controller 58 to thereby control movement and position of the reflector 26.

It should be noted that the arrangement of FIG. 5 illustrates a reflector 26 that is movable/oscillatable through the application of electrical forces by comb drives. However, it should be noted that electrical/electrostatic forces can be applied in a variety of manners besides comb drives. Moreover, beside electrical/electrostatic forces, various other forces may be utilized to drive the movement/oscillation of the reflector 26, such as magnetic, piezoelectric, or combinations of these drivers.

The range of motion of the reflector 26 can be selected as desired, but in one embodiment the reflector 26 is pivotable about the axis 38 at least about 60 degrees, and the reflector 26 is pivotable about the axis 40 at least about 60 degrees, or in another case at least about 40 degrees (with all angles being full angle values representing the full range of motion of the reflector 26). The reflector 26 may guide the beam 22 to define a field of view or field of scan, which is the angular extent of the area illuminated by the scanned beam. It should be noted that the displayed image may be less than the field of view.

In one embodiment the reflector 26 is moved such that the reflector 26 has a significantly higher frequency about one axis than about the other axis. For example, in one embodiment the reflector 26 is moved such that it has a frequency about the axis 40 that is at least about fifteen times greater, up to about 600 times or even greater, than the frequency of oscillation about the axis 38. In one embodiment the reflector 26 may have a frequency of about 19 kHz about the axis 40, and about 60 Hz about the axis 38.

Figure 6:
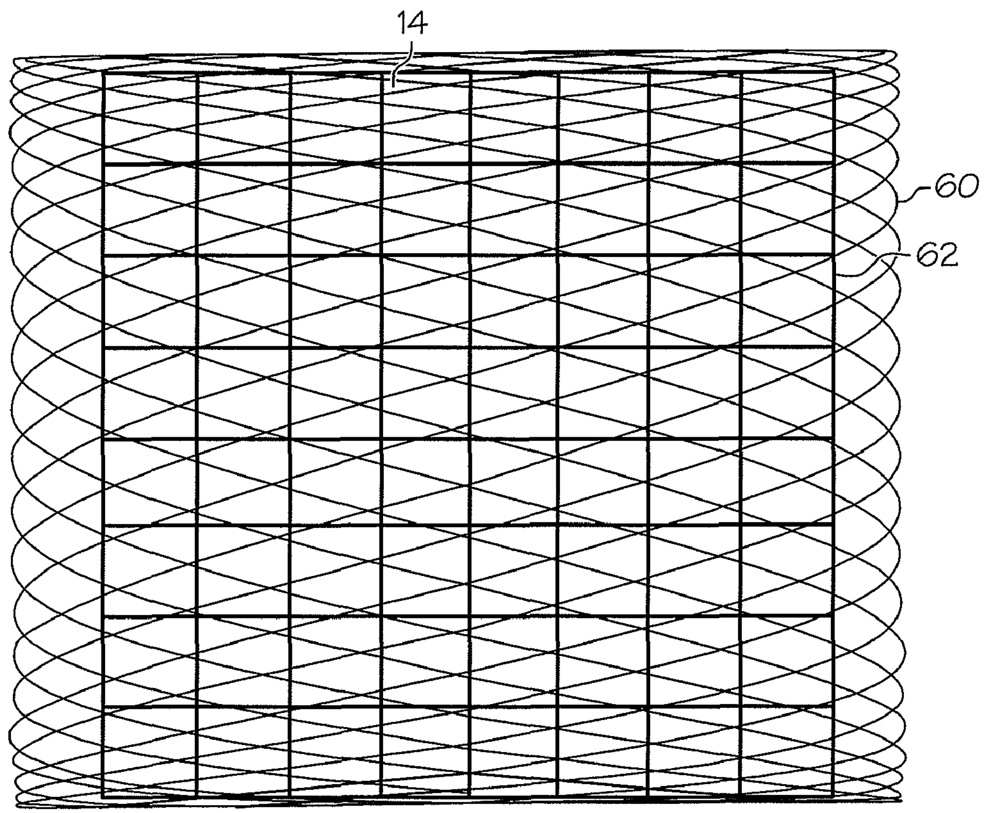
FIG. 6 is a representation of a path of scanned radiation provided by the scanning assembly of FIG. 1.

The reflector 26 may be moved about each axis 38, 40 in a reciprocating motion having a velocity profile that is generally sinusoidal to provide a bi-sinusoidal scan pattern. However, the velocity profile need not necessarily be at or close to sinusoidal. Furthermore, the reflector 26 may be oscillated at or close to resonant frequency about each axis 38, 40 (i.e. in a dual resonant manner). However, the frequency of oscillations can be at nearly any desired value to allow the reflected beam 22 to scan across the illuminated area 14 in the desired manner (such as in a progressive scan pattern). For example, FIG. 6 illustrates a classical Lissajous pattern 60 (imposed upon a grid 62) which may be scanned upon an area 14 during operation of the scanning unit 12. However, the scan pattern need not necessarily be implemented by a progressive scan pattern. Instead, the scan pattern can take any of a variety of other shapes or forms, including a spiral pattern scanned by a flexible or movable optical fiber, or nutating mirror assembly, or other mechanism such as a vibrating optical fiber.

The scanning unit 10 includes a collector 64, which collects/senses radiation emitted by the scanning unit 12 that is returned from the illuminated area 14. In the embodiment of FIG. 1 the collector 64 is configured coaxially within the housing 16 (see also FIG. 2). However, the collector 64 may take a variety of shapes and forms, and also need not necessarily be physically coupled to the housing 16. Since the image of the illuminated area 14 is constructed from the point of view of the "illuminator" (i.e. the reflector 26), the position at which the radiation is collected does not affect the geometry of the image. For example, as the collector 64 is moved, the shapes of the images or structures in the illuminated area 14 may become more or less visible, or even change from visible to not visible, but the geometry of the shapes, and their spatial relationship, remains unchanged. However, movement of the collector 64 may affect the quality of the image. Thus in any case the collector 64 should be located sufficient close to the illuminated area 14 to effectively detect perturbed radiation.

The collector 64 may take any of a variety of forms, and in one embodiment includes a plurality of small diameter, multimode collecting fibers. The ends of the fibers may be polished and arranged in a generally planar manner (or otherwise) to define an aperture. When the reflector 26/scanning unit 12 directs radiation 22 at the area 14, returned radiation impinges on the aperture, and the collecting fibers then conduct the received radiation to a radiation detector assembly 64. The radiation detector assembly 66/controller 58 may be operatively coupled to an image processor 67, which is in turn coupled to a display device 68 (such as a display screen, television screen, monitor, etc.) that can display a visual representation (a video image) of the illuminated area 14 based upon data provided by the collector 64.

Figure 7:
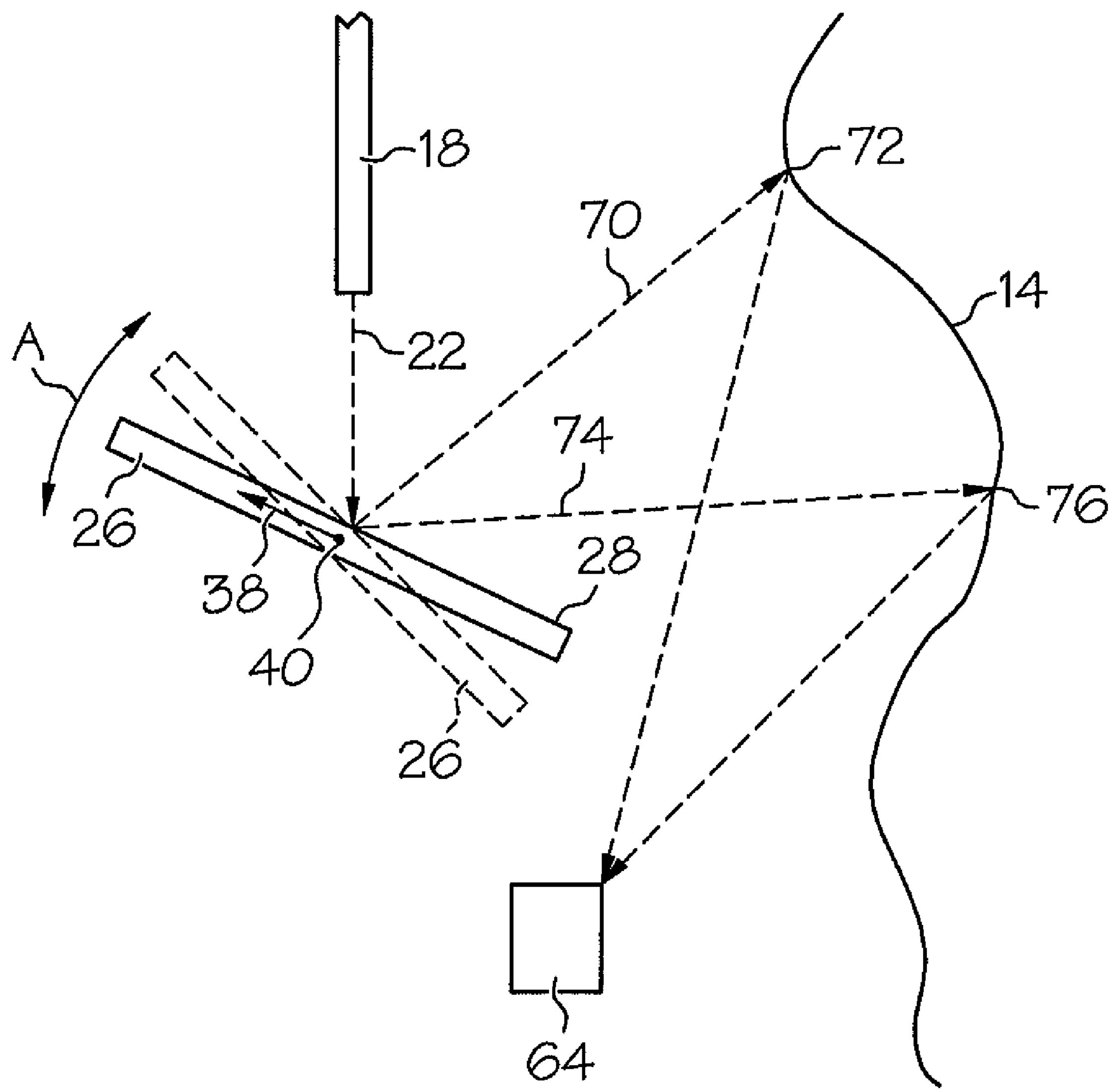
FIG. 7 is a schematic representation of radiation reflected by a reflector at two different positions.

FIG. 7 schematically illustrates the operation of the reflector 26 in conjunction with the collector 64. The reflector 26 receives a beam of radiation 22 from the source fiber 18 and uses its reflective surface 28 to direct the beam 22 onto a surface or illuminated area 14. At a first point in time, the beam 22 deflected by the reflector 26 is in a position shown as 70, and impinges upon the surface to illuminate point 72. As the reflector 26 moves or oscillates about axis 40 (indicated by arrow A) at a later point in time the beam is in the position shown as 74 where the beam illuminates point 76. The directed radiation is reflected, absorbed, scattered, refracted or otherwise affected by the filed of view 14, at least some of which is detected by the collector 64. The perturbed radiation may leave the area 14 in many directions and thus the collector 64 may only capture that fraction of reflected radiation which reaches its aperture.

Figure 2:
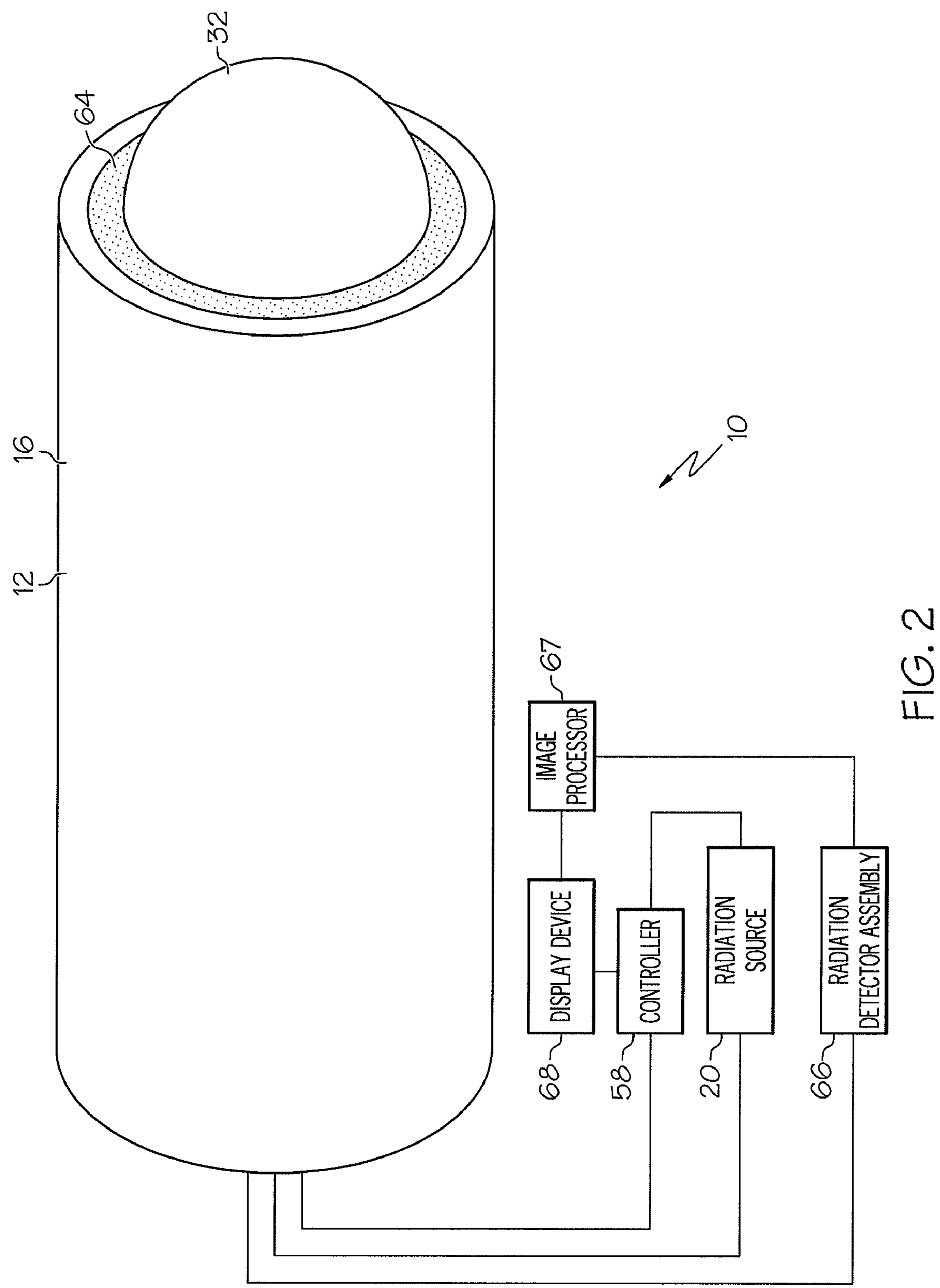
FIG. 2 is a front perspective view of the scanning assembly of FIG. 1.

Referring also back to FIGS. 1 and 2, radiation that is intercepted by the collector 64 is passed to the radiation detector assembly 66. The radiation detector assembly 66 may take the form of or include a bolometer, photodiode or avalanche photodiode that can output a series of electrical signals corresponding to power, amplitude, or other characteristic of each wavelength of radiation detected. The radiation detector assembly 66 may include, or be coupled to, an analog-to-digital converter to convert the image data into a digital image signal stream. The signals can be used/processed by the image processor 67 (which could be, in one embodiment, part of the controller 58) to generate an image of the illuminated area 14 which can be displayed on a display device 68, or printed, stored, or further processed. The image can be generated by taking into consideration, for example, the position, angle, intensity and wavelength of beam 22 directed by the reflector 26, and the amount and/or wavelength of radiation sensed by the collector 50.

The housing 16 may constitute or include an elongate shaft (which can be either rigid or flexible) that is insertable into the body of a patient. The radiation source 20, controller 58, radiation detector assembly 66, image processor 67 and display device are 68 typically not insertable into the patient or carried in the housing 16, but are instead typically components positioned outside the body and accessible for use and viewing.

Figure 8:
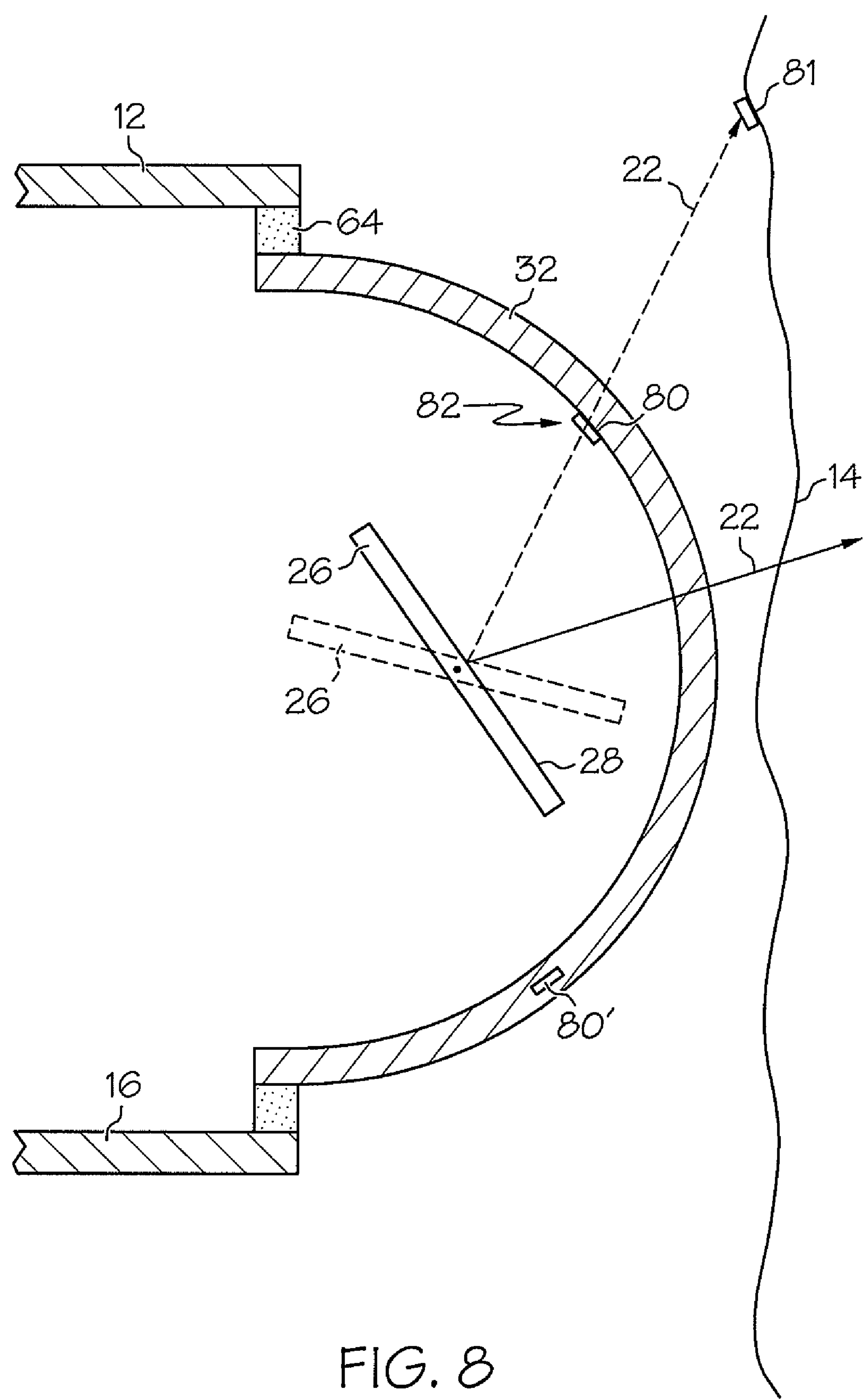
FIG. 8 is a side cross section of the distal end of the scanning assembly of FIG. 1, illustrating various reference marks.
Figure 9:
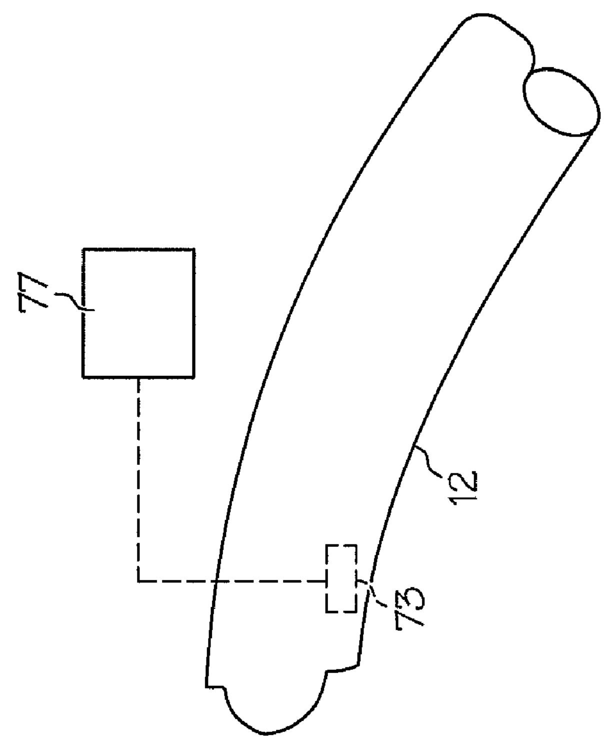
FIG. 9 is an embodiment of a scanning assembly including a system for controlling operation of the scanning assembly.
Figure 9:
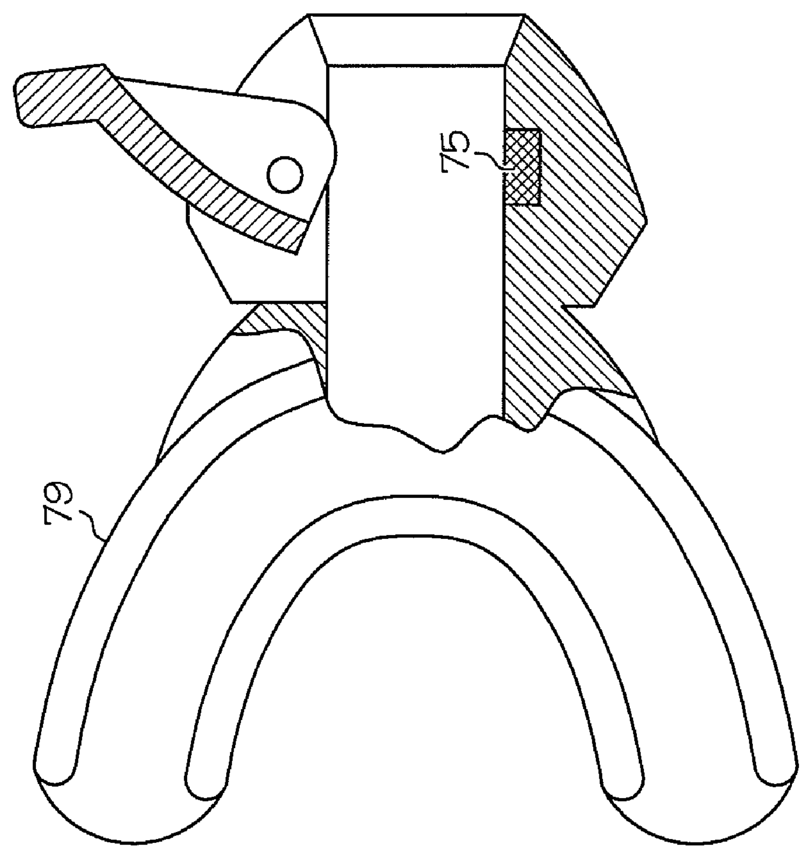

In certain cases, it may be desired to provide a reference mark 80 or marker positioned to reflect the beam of radiation after the beam reflects off of the reflector 26, but before the beam impinges upon the area of interest 14. For example, as shown in FIG. 8, a reference, also known as an auto correction marking ("ACM"), is positioned on the inner surface of the optical element 32. The reference mark 80 can have any variety of indicia, designs, patterns or the like (collectively termed "indicia" herein) printed, positioned, or otherwise formed or located thereon. FIG. 9 illustrates some examples of indicia that may be carried by the reference mark 80. The indicia may be composed of high contrast patterns, geometric shapes or other forms of a type not expected to be found in the area of interest 14 to allow easy identification of the reference mark 80. The indicia of the reference mark 80 may include portions that are generally opaque to the radiation. The reference mark 80 can aid in tracking the position of the reflector 26, and thereby providing accurate reconstruction of the scanned image. Various details of use of a reference mark 80 are described in pending U.S. patent application Ser. No. 11/845,457, filed Aug. 27, 2007, entitled POSITION TRACKING AND CONTROL FOR A SCANNING ASSEMBLY, the details of which are hereby incorporated by reference as if fully set forth herein.

In the embodiment of FIG. 8, the reference mark 80 is positioned on the inner surface of the optical element. The reference mark 80 is shown in FIG. 8 illustrates another position wherein the reference mark 80 is formed in, or embedded in, or laminated on, the optical element. The reference mark 80 can also be positioned on an outer surface of the optical element, or at other positions between the reflector and the area of interest 14. The reference mark 80 may thus be positioned such that the radiation beam impinges upon the reference mark 80 before the beam entirely passes through the optical element.

In some embodiments, it may be desirable to provide one or more automated systems for controlling radiation output, for example, based on location of the scanning unit 12 and/or operating conditions of the reflector 26. Additionally, organizations like the International Electrotechnical Commission (IEC) and the American National Standards Institute (ANSI) provide standards that apply to manufacturers and users of laser devices, for example, setting forth eye and skin Maximum Permissible Exposure (MPE) values. The MPE is the maximum power or energy density (in $J/cm^2$ or $W/cm^2$) exposure to a light source determined by one or more of these organizations. For example, if the scanning unit 12 is not located within the desired body cavity, it may be desirable to prevent unintended output of certain power levels until the scanning unit is within the desired body cavity. As another example, if the reflector 26 is not scanning properly, it may be desirable to detect this condition to prevent output of unintended doses of radiation.

Referring again to FIG. 1, the scanning assembly 10 may include a system, generally referred to as element 71, that automatically limits a power level of the radiation source 20 when the scanning unit 12 is outside the intended cavity. In some embodiments, the system 71 includes a magnetically actuated switch 73 that is used to control operation of the radiation source 20. The magnetically actuated switch 73 is responsive to a magnetic field, which is used to toggle the switch between states. For example, a first state of the magnetically actuated switch 73 may indicate that high power is available and another state may indicate that high power is not available. In other words, the magnetically actuated switch 73 can be used to limit output power of the scanning assembly 10 when the magnetically actuated switch is in its first state.

Referring to FIG. 9, in some embodiments, the magnetic field may be provided by a magnet 75 that is associated with an instrument to facilitate insertion of the scanning unit 12 into the body. For example, the magnet 75 may be carried by a stabilizer 79 for stabilizing the scanning unit 12 when inserted into a natural orifice, such as the mouth of a patient. As another example, the magnet 75 may be carried by a trocar, such as that commercially available from Johnson & Johnson Gateway, LLC for artificial ports. As the shaft of the scanning assembly 10 is passed from its distal end to a proximal location through the opening, an insertion is registered due to the magnetic field provided by the magnet 75, for example, by a controller and high power is enabled. As the shaft of the scanning assembly 10 is passed from its proximal location to its distal end through the opening, a removal is registered and high power operation is disabled. In some embodiments, an external accessory 77 is provided to reset the magnetically actuated switch 73 to the state that disables high power operation, for example, that can be operated using input from an operator. In some implementations, the accessory 77 allows the operator to place the magnetically actuated switch 73 in the state that enables high power operation.

Figure 10:
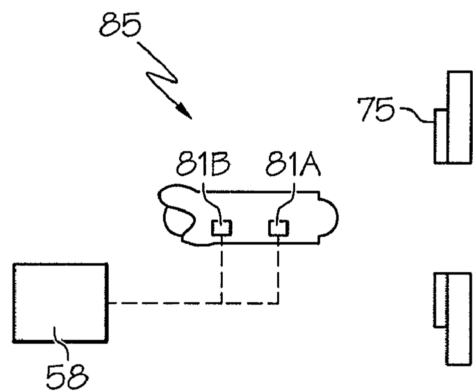
FIG. 10 is another embodiment of a scanning assembly including a system for controlling operation of the scanning assembly.

FIG. 10 shows another embodiment 85 where multiple sensors 81A and 81B, such as Hall sensors, are provided to distinguish between whether the scanning unit 12 is being inserted or retracted. The sensors 81A and 81B provide a signal in response to a magnetic field and are connected to a controller/processor 58 that includes logic for distinguishing between an insertion or retraction. As can be seen, sensor 81A is located distally of sensor 81B on the housing 16 such that if controller/processor 58 (FIG. 1) receives a signal from sensor 81A, then 81B, an insertion is identified and high power is enabled. Conversely, if the controller/processor 58 receives a signal from sensor 81B, then 81A, a retraction is identified and high power is disabled.

It should be noted that the magnetically actuated switch/sensors can have a limited range of detection of the magnet. For example, the switch/sensors may be capable of detecting the magnet over a range of about ⅛ to 1 inch, such as about ¼ inch. The state of the switch may be stored, for example, in memory or in another component such as a latch.

While magnetically actuated sensors are described above, other sensor types may be used, such as impedance sensors, capacitive sensors, etc. Additionally, mechanical approaches may be utilized such as a ratcheting system in combination with a magnetic switch, where the ratcheting system temporarily locks the magnetic switch in a particular state as the switch is passed by the magnetic field. In certain implementations, a magnetically latching device may assume the first state upon passing the magnet 75 in one direction (e.g., an insertion) and assume the second state when passing the magnet in another direction (e.g., a retraction). In certain embodiments, multiple magnetically actuated devices may be employed for backup and robustness. In some embodiments, the system 71, 85 may be calibrated, such that when the scanning assembly 10 is turned on, it is assumed the scanning unit 12 is outside the intended cavity and high power is not enabled by default. A user override may be provided and used to enable high power manually.

While the above description relates to determining if the scanning unit 12 is located within the desired cavity or enclosure, it may be desirable to determine whether or not the reflector 26 is scanning properly. A loss of scan condition of the reflector 26 can result in unintended radiation doses being delivered to tissue. Various systems may be utilized to detect a loss of motion condition of the reflector 26. As will be noted below, some systems may use the reference mark, however, other systems may not. In some embodiments, the reference mark 80 may be used because the image processor 67 continuously monitors the received data stream for the characteristic signature of the reference mark 80, a persistent lack of such signature can imply that the reflector 26 is no longer moving as intended (i.e., a loss of scan condition is present). In such event, the radiation source 20 can be commanded to terminate emissions of the radiation beam.

Figure 11:
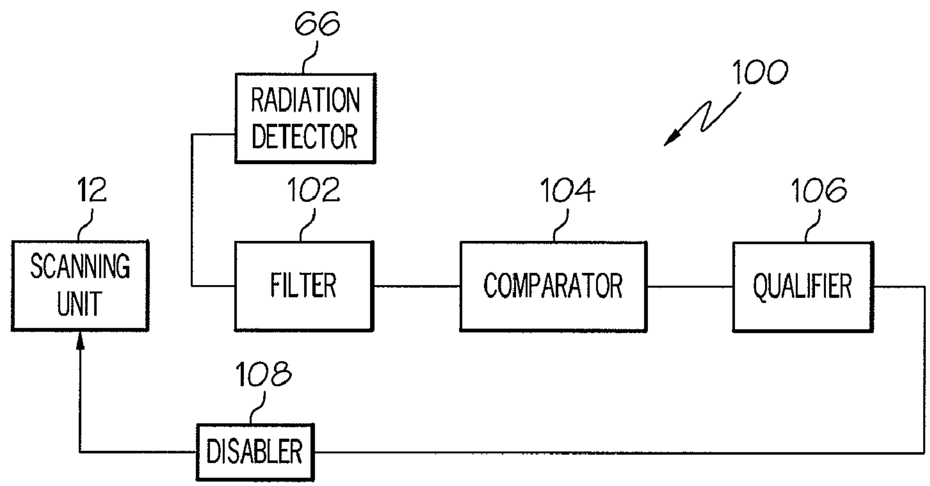
FIG. 11 is an embodiment of a system for detecting a loss of scan condition of the reflector.

Referring now to FIG. 11, a system 100 for detecting a loss of scan condition utilizes the signal produced by the radiation detector assembly 66 to detect the loss of scan condition. The signals include spectral components at harmonics of the scan frequencies. The system 100 utilizes the expected periodic structure of the signals to determine whether the reflector 26 is scanning. If the scanning of the reflector 26 stops, then the spectrum of the output collapses, i.e., the value of the signal becomes a constant, for example, zero or some other constant. The system 100 looks for lines in the spectrum not at the constant. If those lines disappear, then it may be the case that the reflector 26 has stopped scanning. Other possibilities are that the receive system is not operating properly or that there is no beam being generated. In some embodiments, the system 100 can distinguish between these possibilities. For example, the system 100 may also monitor the radiation source 20 and/or monitor the beam of radiation output by the radiation source before it passes to the reflector 26 to identify whether no beam is being generated.

The system 100 includes a filter 102 that is used to filter the signals from the radiation detector assembly 66, for example, prior to subjecting the signals to any nonlinear processing. In some embodiments, the filter 102 is a bandpass filter that passes frequencies within a certain range and rejects frequencies outside that range. For example, a low end of the range may be set above frequencies resulting from manual movement of the scanning unit 12 with the reflector 26 stationary (i.e., above frequencies one might expect from a user swinging the scanning unit 12 should the reflector 26 stop scanning). The upper end of the range may be set at least high enough pass frequencies associated with the system's highest resolution, which may be governed by the diameter of the beam and the electrical bandwidth of the detectors and amplifiers.

As another example, the filter 102 may be a comb filter that adds a delayed version of the signal to itself, causing constructive and destructive interference thereby providing a periodic response in frequency. The comb filter can have a large number of passbands that are centered on frequencies at which the spectrum has energy. In some embodiments, a bandpass filter (or separate low and high-stop filters) may also be included to filter out extreme low and high frequencies.

It should be noted that while the above system 100 looks for conditions expected when the reflector 26 is scanning, the system could look for conditions expected when the reflector is not scanning. For example, the filter 102 may be a low-pass filter that allows only those low frequencies to pass that would be expected should the reflector 26 stop scanning. Additionally, the reference mark 80 may be utilized for providing the spectral components. For example, the filter 102 may be a matched filter that responds maximally to the signal corresponding to the structure of the reference mark 80.

The system 100 includes a comparator 104 that compares the magnitudes of the output of the filter 102 against a limit. The limit may vary with operating conditions, scene, etc. When the output drops below the limit, then a qualifier 106 determines whether the reflector 26 has stopped scanning. In some embodiments, the qualifier 106 ignores brief low outputs, which may occur for reasons other than loss of scanning. If the qualifier 106 determines there is a loss of scan condition, then a laser disable input 108 (e.g., incorporated in the controller 58, source 20 or separate component) shuts down the radiation source. In some embodiments, the laser disable input 108 may operate a beam blocker, such as part of an external treatment system. In some embodiments, the processor 58 may include the comparator 104 and qualifier 106.

Figure 12:
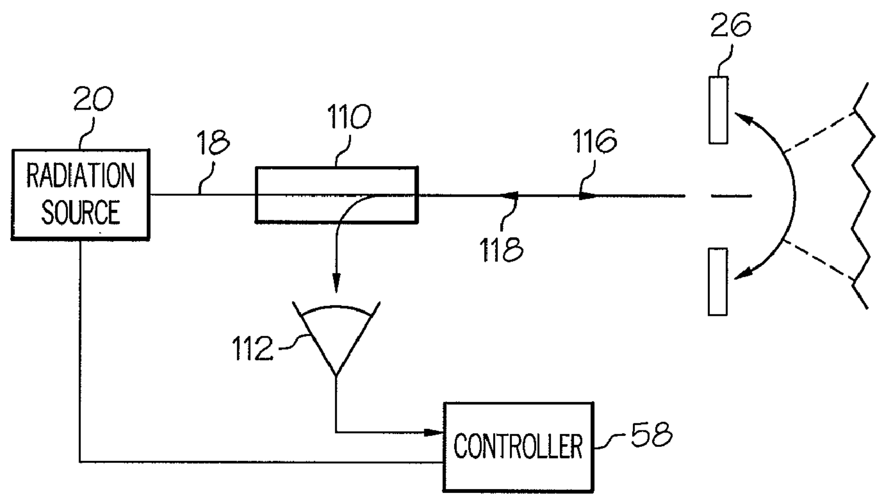
FIG. 12 is another embodiment of a system for detecting a loss of scan condition of the reflector.

FIG. 12 shows an alternative embodiment in which radiation reflected and returning through the source fiber 18 is used to detect a loss of scan condition. As the outgoing beam 116 is scanned across the area of interest, some of the radiation makes its way back into the source fiber 18 in the form of a return beam 118. A fiber optic coupler 110 is used to separate the return 118 beam from the source fiber 18 and direct the return beam to a detector 112. The detector 112 provides an output to the processor 58, which monitors the output to determine whether the reflector 26 is scanning and interrupts the outgoing beam should the determination be made that scanning has stopped.

As one example, the processor 58 looks for temporal signal variations in the output of the detector 112. When the reflector 26 is oscillating, the change in scene reflectance as the scanned beam is reflected by varying tissue, structures and surface angle causes a variation of radiation reflected back into the source fiber 18 in a somewhat unpredictable way, however, the temporal frequency content will be different if the scanner is scanning versus stopped. Thus, if there are temporal signal variations at unexpected frequencies, then the frequency content can be analyzed to determine if the reflector is likely to be scanning. The absence of such temporal signal variations can be interpreted as an indication of a loss of scan condition and the radiation source 20 can be shut down in response.

As another example, the reference mark 80 could be applied to the dome surface at a position that is outside the area of interest and outside the acceptance angle of the collector, but at a position that can be interrogated by the outgoing beam 116. The reference mark 80 can provide a repeatable reflection signature as the mirror oscillates, which is recognized by the processor 58. The absence of this repeatable reflection signature can be interpreted as an indication of a loss of scan condition and the radiation source 20 can be shut down in response.

Figure 13:
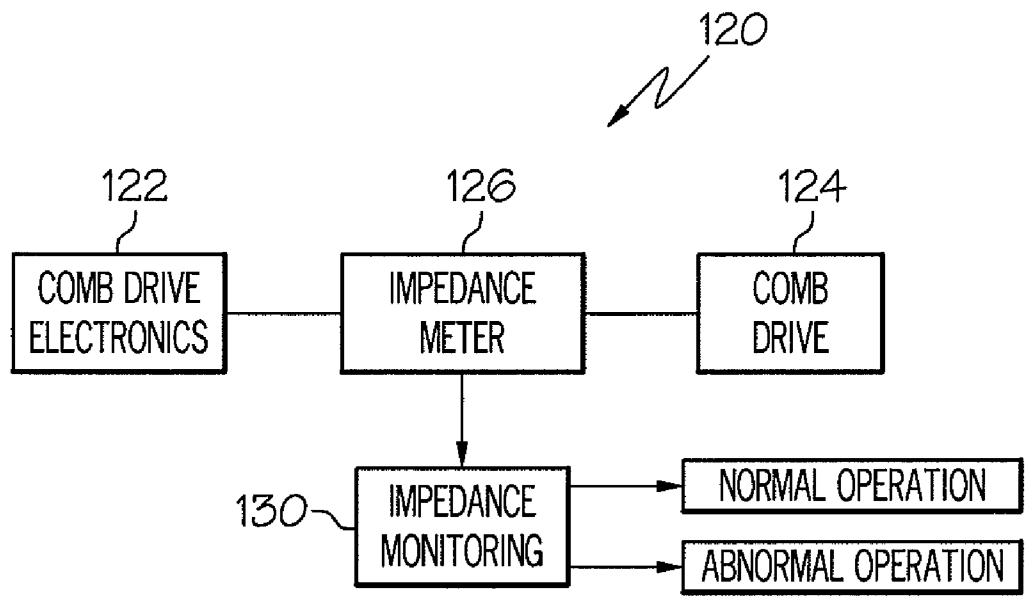
FIG. 13 is another embodiment of a system for detecting a loss of scan condition of the reflector.

Referring now to FIG. 13, as indicated above, the reflector 26 can be moved employing comb drives. The comb drives can be operated at or near the mechanical resonant frequency to achieve minimum operating currents (i.e., at or near the maximum system impedance). Once stable operation is established, impedance at the operating frequency is constant or slowly varying (as a function of temperature). This slowly varying change in impedance can be used to alter the drive frequency as the resonant frequency shifts.

Figure 14:
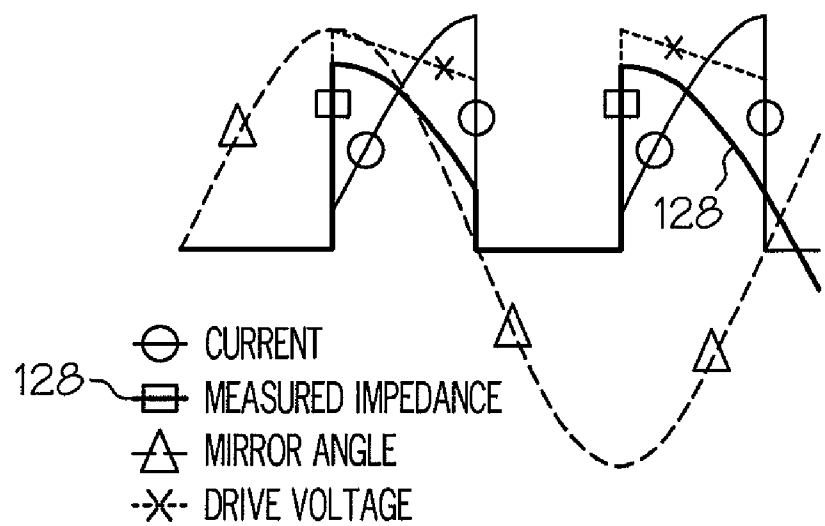
FIG. 14 is an exemplary plot of various waveforms.

For large-scale disruption of operation such as a loss of a comb finger, jammed comb fingers, failed hinges, massive comb dislocation, etc. rapid changes in the impedance waveform (FIG. 14) can be expected. For example, in some instances, disruption of operation of the comb drive 124 will result in a change in the mean value of the impedance. Once this mean value of the impedance changes, this changed steady-state value can indicate a loss of scan condition. In some instances, disruption of operation of the comb drive will change the periodic variation of impedance (e.g., it will become non-periodic) or will take a different value that can be detected, which can indicate a loss of scan condition.

FIG. 13 shows a block diagram of a system 120 to detect a loss of scan condition using comb drive impedance measurements. The system 120 includes comb drive electronics 122, which contains all the electrical components required to generate the desired signal to cause activation of the comb drive 124, such as power supplies, amplifiers, active analog feedback circuits, waveform generators, digital control functions, etc. The comb drive electronics 122 causes creation of a voltage waveform similar to that shown by FIG. 14, which is only one example from a large number of waveforms that could be generated. In the case of the electrostatic comb drive 124, the voltage is applied only at a time when the reflector 26 is off-center and in synchrony with the angular displacement of the reflector and turned off just prior to crossing the center, or zero position.

The impedance of the comb drive 124 is dominated by the capacitance between the stationary and moveable portions of the comb drive. Generally, capacitance can be computed by $$C = \varepsilon\frac{A}{d},$$

where ∈ is the dielectric constant of the material between the comb fingers, A is a measure of the area of the fingers and d is the distance between the comb fingers. For practical systems, the projected area between the fingers is a function of rotational angle between the stationary and moving portions of the comb drive and can be approximated, to the first order, as a cosine function with zero radians being defined as the angle between the stationary and moving portions when they are coplanar. The impedance is at its maximum value (minimum capacitance) when the reflector 26 is at its largest deflection angle and at its smallest when the reflector is centered (zero degrees). In the centered state, there is a dielectric separating the stationary and moving portions of the comb drive and this is the maximum capacitance (minimum impedance) position and it is non-zero. Currents can be measured, and thus impedance calculated for the conditions specified above.

Referring still to FIG. 13, an impedance meter 126 measures the instantaneous impedance of the drive combs it is connected to. During normal operation, a series of time varying impedances, similar to those shown by FIG. 14 where trace 128 occurs at the period of the oscillatory period of the reflector 26. Should the reflector 26 be jammed or otherwise stop moving, there will be no change in capacitance and therefore no change in impedance during the non-zero portion of the drive waveform. The output of the impedance meter 126 is a signal (analog or digital) corresponding to the impedance of the comb drive. An impedance monitoring element 130 accepts the output from the impedance meter 126 and determines if the comb drive is operating normally or it there is a loss of scan condition. The impedance meter can make rapid measurements of the impedance (e.g., many measurements per cycle of the reflector's movement in either axis) and provide an output to the impedance monitoring component 130 indicative of these measurements.

The impedance monitoring element 130 may include low and high pass filters. The low pass filter is constructed to provide an affirmative output if the rate of change of the instantaneous impedance measurements are small, likely indicating a loss of scan condition. The high pass filter may be constructed to provide an affirmative output if the rate of change of the instantaneous impedance measurements are large, likely indicating normal operation.

Such filters may be implemented in analog (continuous time) or digital (discrete time) form. As examples of digital implementations, Finite Impulse Response (FIR) filters of Infinite Impulse Response (IIR) filters could be used. In some embodiments, a conversion of the data stream to the frequency domain using a Fourier Transform (DCTs of FFTs) and then looking for threshold values in appropriate frequency bins could be used.

Figure 15:
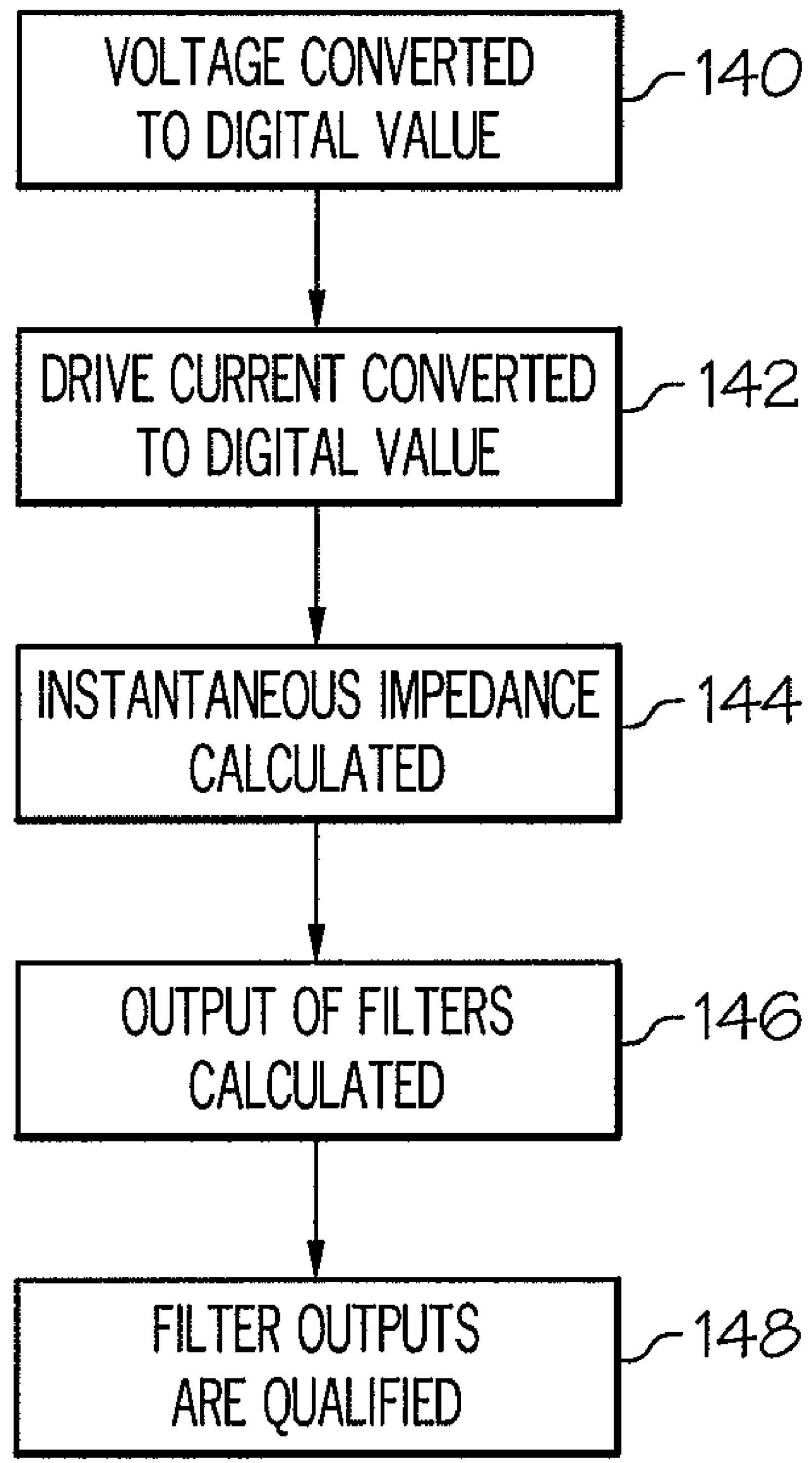
FIG. 15 is an embodiment of a method for detecting a loss of scan condition using the system of FIG. 13.

One digital implementation of the impedance metering and monitoring functions of FIG. 13 is illustrated in FIG. 15. The voltage applied to the comb drive is converted to a digital value at a rate of at least two times the highest frequency component of interest in the drive waveform at step 140. At step 142, the drive current is converted to a digital value at the rate specified in step 140. Steps 140 and 142 may occur at the same time, although they are shown separately. The instantaneous impedance is calculated at each of the sample points at step 144. The output of the high and low pass filters is calculated in step 146. At step 148, the filter outputs are further qualified (for example, a transient condition caused by noise should be rejected, and nonmeaningful combinations of filter outputs ignored) and output. The qualified output signals are presented for use in the system, for example to present status or alarm information to the user, and to shut down the source or block the output beam in the event of a fault. In some embodiments, the A/D converters, clock generators, computational and logic elements involved in these steps are all part of a single integrated circuit.

While the present invention has been illustrated by a description of several expressions of embodiments, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended claims.

What is claimed is:

1. A method of controlling a medical device, the method comprising:

generating a beam of radiation using a radiation source assembly;

directing the beam of radiation toward a distal end of the medical device using an optical fiber;

directing the beam of radiation onto an area of interest by scanning a reflector in a scanning pattern, the reflector receiving the beam of radiation from the optical fiber;

collecting radiation from the area of interest using a collector;

detecting the collected radiation; and detecting a loss of scan condition of the reflector automatically using a control system by examining a periodic structure of the detected radiation, wherein the loss of scan condition is detected based upon deviations from an expected periodic structure of the detected radiation.

2. The method of claim 1 comprising interrupting the beam of radiation if a loss of scan condition is detected by the control system.

3. The method of claim 1 comprising disabling the radiation source assembly if a loss of scan condition is detected by the control system.

4. The method of claim 1 further comprising:

separating collected radiation received by the distal end of the optical fiber and traveling proximally through the medical device from the beam of radiation directed toward the distal end of the medical device;

wherein detecting the collected radiation comprises detecting the separated and collected radiation received by the distal end of the optical fiber; and wherein detecting a loss of scan condition comprises comparing temporal signal variations in the detected radiation to expected temporal signal variations at harmonics of the scan frequencies to detect the loss of scan condition.

5. The medical device of claim 4 wherein the absence of temporal signal variations is interpreted as an indication of a loss of scan condition.

6. The medical device of claim 4 wherein a temporal signal variation at an unexpected frequency is interpreted as an indication of a loss of scan condition.

7. The method of claim 1 wherein the collector is arranged and configured to pass the collected radiation to a radiation detector, the radiation detector outputting a signal corresponding to a characteristic of the radiation for use in producing a viewable image, the control system performing the steps of filtering the outputted signal with a filter responsive only to frequency components of the outputted signal to produce an output based on at least one predetermined range of frequency components of the outputted signal; and detecting the loss of scan condition of the reflector using a comparator, the comparator comparing the magnitude of the filtering step output against a limit.

8. The medical device of claim 7 wherein the filtering step adds a delayed version of the outputted signal to itself.

9. A medical device, comprising:

a radiation source assembly including a radiation source configured to generate a beam of radiation;

an optical fiber that directs the beam from the radiation source assembly toward a distal end of the medical device;

a reflector that receives the beam from the optical fiber, the reflector configured to direct the beam onto an area of interest by scanning in a scanning pattern;

a collector arranged and configured to receive radiation from the area of interest and to pass received radiation to a radiation detector, wherein the radiation detector outputs a signal corresponding to a characteristic of the received radiation for use in producing a viewable image;

a filter responsive only to frequency components of the outputted signal, wherein the filter is configured to produce an output based on at least one predetermined range of frequency components of the outputted signal;

a comparator adapted to provide an indication when the output of the filter exceeds or is below a predetermined limit; and a qualifier adapted to examine temporal variations in the indication of the comparator, wherein the temporal variations are analyzed to determine if the reflector has stopped scanning.

10. The medical device of claim 9, wherein the radiation source assembly includes at least two radiation sources, the optical fiber being arranged and configured to receive an imaging beam and a therapeutic beam generated by the at least two radiation sources.

11. The medical device of claim 9 further comprising a controller that allows or inhibits output of the beam by the radiation source assembly based on the indication of the qualifier.

12. The medical device of claim 9, wherein the filter is selected from a high pass filter, a low pass filter and/or a band pass filter.

13. The medical device of claim 9, wherein the filter comprises a comb filter.

14. The medical device of claim 9 further comprising a reference mark positioned such that the beam of radiation from the radiation source is selectively directed at the reference mark.

15. A medical device, comprising:

a radiation source assembly including a radiation source configured to generate a beam of radiation;

an optical fiber that directs the beam from the radiation source assembly toward a distal end of the medical device along a path defined by the optical fiber;

a reflector that receives the beam from the optical fiber, the reflector configured to direct the beam onto an area of interest by scanning in a scanning pattern;

a collector arranged and configured to receive radiation from the area of interest and to pass received radiation to a radiation detector, wherein the radiation detector outputs a signal corresponding to a characteristic of the received radiation for use in producing a viewable image;

a beam splitter arranged and configured to separate reflected radiation returning through the optical fiber from the distal end of the medical device toward a proximal end of the medical device from the beam of radiation, wherein the beam splitter directs the reflected radiation to a return beam detector; and a processor adapted and configured to examine temporal signal variations in an output of the return beam detector, wherein the temporal frequency content of the signal variations is analyzed to determine if the reflector is scanning

16. The medical device of claim 15 further comprising a controller configured to monitor the reflected radiation separated by the beam splitter from the path to determine a loss of scan condition of the reflector.

17. The medical device of claim 16 further comprising a reference mark positioned such that the beam of radiation from the radiation source is selectively directed at the reference mark, the reflected radiation traveling through the optical fiber including radiation reflected from the reference mark.

18. The medical device of claim 17, wherein the beam of radiation generated by the radiation source assembly is interrupted by the controller if a loss of scan condition is detected.

19. The medical device of claim 15, further comprising:

a control system configured to control the radiation source by detecting an insertion or retraction of the medical device into a body cavity.

20. The medical device of claim 19, wherein the control system comprises a magnetically actuated switch having a first state that allows the medical device to output the beam and a second state that prevents output of the beam, the magnetically actuated switch being responsive to a magnetic field.

21. The medical device of claim 20, wherein the magnetic field is generated by a magnetic component associated with an opening to the body cavity through which the medical device is inserted.

* * * * *